(12) United States Patent
Storer et al.

(10) Patent No.: US 6,758,864 B2
(45) Date of Patent: Jul. 6, 2004

(54) CEMENTLESS PROSTHETIC BEARING ELEMENT

(75) Inventors: John Andrew Storer, Munich (DE); Richard Eddy Field, Surrey (GB); Neil Rushton, Cambridge (GB)

(73) Assignee: Benoist Girard SAS (FR)

( * ) Notice: Subject to any disclaimer, the term of this patent is extended or adjusted under 35 U.S.C. 154(b) by 0 days.

(21) Appl. No.: 10/010,893

(22) Filed: Nov. 5, 2001

(65) Prior Publication Data

US 2002/0107577 A1 Aug. 8, 2002

(30) Foreign Application Priority Data

Nov. 7, 2000 (GB) ............................................ 0027211

(51) Int. Cl.⁷ .................................................. A61F 2/34
(52) U.S. Cl. ................................ 623/22.38; 623/22.21; 623/22.15
(58) Field of Search .......................... 623/22.11, 22.15, 623/22.21, 22.38, 22.32

(56) References Cited

U.S. PATENT DOCUMENTS

| | | | |
|---|---|---|---|
| 2,910,978 A | 11/1959 | Urist | |
| 3,840,904 A | 10/1974 | Tronzo | |
| 3,882,550 A | * 5/1975 | Karpf et al. | 623/22.39 |
| 3,903,549 A | * 9/1975 | Deyerle | 623/22.36 |
| 4,743,262 A | 5/1988 | Tronzo | |
| 4,790,851 A | 12/1988 | Suire et al. | |
| 5,181,930 A | 1/1993 | Dumbleton et al. | |
| 5,358,532 A | * 10/1994 | Evans et al. | 623/22.23 |
| 5,443,513 A | 8/1995 | Moumene et al. | |
| 5,609,646 A | 3/1997 | Field et al. | |
| 5,879,387 A | 3/1999 | Jones et al. | |
| 5,879,406 A | 3/1999 | Lilley | |
| 5,904,720 A | 5/1999 | Farrar et al. | |
| 6,126,695 A | 10/2000 | Semlitsch | |
| 6,221,108 B1 | 4/2001 | Smith | |
| 2001/0027345 A1 | 10/2001 | Merrill et al. | |

FOREIGN PATENT DOCUMENTS

| | | |
|---|---|---|
| DE | 44 37 479 A1 | 2/1996 |
| FR | 2 635 968 | 3/1990 |
| WO | WO 99/03429 | 1/1999 |

* cited by examiner

*Primary Examiner*—Cary E. O'Connor
*Assistant Examiner*—Candice C. Melson
(74) *Attorney, Agent, or Firm*—Lerner, David, Littenberg, Krumholz & Mentlik, LLP

(57) ABSTRACT

The present invention is intended to provide a cementless prosthetic bearing element which has been molded and which is possible to place in an acetabular socket without cement, the outer surface of the backing being provided with elements to assist stabilization and the ingrowth of bone. Thus, the bearing element is cheaper and easier to produce and provides superior location and installation in the bone. According to the present invention a cementless prosthetic bearing element comprises a backing which supports a bearing liner having a bearing surface, the backing being molded from a rigid polymeric material and said bearing liner being made from elastomeric polyurethane material to which the backing is molded with an outer surface which includes a number of raised engagement features provided in directions extending away from and/or towards the outer periphery of the outer surface.

28 Claims, 2 Drawing Sheets

CEMENTLESS PROSTHETIC BEARING ELEMENT

BACKGROUND OF THE INVENTION

This invention relates to a cementless prosthetic bearing element. More particularly it relates to a cementless prosthetic acetabular cup.

At the present time wear of the well known polyethylene acetabular bearing components in hips, the tibial bearing component in knees, and other prosthetic bearing inserts limits the life of these artificial joints. Normally orthopedic devices for joint construction and reconstruction comprise polyethylene bearings on metal or ceramic, or metal on metal for articulation. The polyethylene bearing is often held in a metal shell, for example in hip constructions or a tray in knee constructions. Conveniently bearing liners made from ultra-high molecular weight polyethylene are fixed via a snap fit into the metal backing.

The possible use of elastomers in bearings to encourage fluid film lubrication at low velocity, and with a low viscosity lubricant such as in a reconstructed joint has been published in laboratory studies which show that such "compliant" bearings provide lower coefficient of friction compared with standard polyethylene versus metal bearings. Soft grades of polyurethane have been shown to be suitable materials for compliant bearings in, for example, EP 0 608382 and U.S. Pat. Nos. 5,879,387 and 6,221,108.

Because of the fluid or thin film lubrication, it is far less likely that the two bearing surfaces touch during use and thus wear is lower. It is however difficult to apply this concept for a number of reasons. One difficulty lies in selecting a polyurethane or other elastomer which will not be degraded by the human body so great care must be taken in selecting compliant bearing material. As mentioned above polyethylene bearing are usually held by physical means in, for example, a metal shell but it is not possible to use this approach with a "compliant" bearing because as its stiffness is so much lower than the metal it would be possible for it to extrude from the shell or be easily moved relative to the shell causing damage. Also lower stiffness would lead to greater interface strain.

Because of the above difficulties, present inventors have tried several different approaches. Initially, for ease of use and conventional appearance, it was attempted to bond a soft grade of polyurethane onto a stiffer polyurethane backing to form a construct similar to pre-existing polyethylene components. This construct could then be assembled in a metal shell or cemented depending on the surgeon's preference and clinical judgment.

The present invention therefore is related to a prosthetic bearing element which uses an elastomeric "compliant" bearing material.

U.S. Pat. No. 5,879,387 describes a bearing element which has a backing made from a rigid polymeric material and a soft elastomeric polyurethane material liner. Bearing elements of this type can be made by a molding process and this is also described.

Similarly, U.S. Pat. No. 5,609,646 describes a process for the manufacture of an acetabular cup of particular configuration and in which the inner bearing component and the backing are molded together to form a single component, the backing being stiffer than the inner bearing component.

It has been found that the use of a molding technique to make such prosthetic bearing elements can be used to advantage to produce elements which have superior qualities and which do not require machining on the external surface of the backing.

It is known, for example from EP 0 297 789 to provide bearing elements of this type which are to be held in place by cement with concentric circumferential and radial grooves to assist in stabilizing and securing the shell stiffener to the layer of cement when the cup is placed in the acetabular socket. It is relatively easy to machine such grooves.

SUMMARY OF THE INVENTION

The present invention is intended to provide a cementless prosthetic bearing element which has been molded and which is possible to place in an acetabular socket without cement, the outer surface of the backing being being provided with elements to assist stabilization and the ingrowth of bone. Thus, the bearing element according to the present invention is cheaper and easier to produce and provides superior location and installation in the bone.

According to the present invention a cementless prosthetic bearing element comprises a backing which supports a bearing liner having a bearing surface, the backing being molded from a rigid polymeric material. The bearing liner is made from elastomeric polyurethane material and to which the backing is molded. The backing has an outer surface which includes a number of raised engagement features provided in directions extending away from and/or towards the outer periphery of the outer surface.

In one preferred embodiment the engagement features are formed by projecting strakes and these can be of substantially triangular cross-section.

The invention can be applied to bearing elements, the outer surface of the backing of which can be of any desired shape, for engagement with the bone concerned and if the element is in the form of an acetabular cup or similar device the outer surface of the backing can be substantially part-spherical and the raised engagement features extend in radial and/or chordal directions.

In order to provide additional stability the outer surface can also carry one or more projecting fins which extend normal to the surface. Such fins can be spaced apart and extend in parallel chordal directions.

It will be appreciated that the time and expense involved in attempting to machine such a surface having the kind of features referred to and such fins is extremely costly and time consuming whereas by applying the molding technique of the present invention they can be formed relatively easily.

The teaching set forth in U.S. Pat. No. 5,879,387, which are incorporated herein by reference, can be applied to the present invention and thus the backing can be made from a "rigid" polymeric material having a minimum hardness value of 65 $N/mm^2$ and the bearing liner can be made from a "soft" elastomeric polyurethane having a hardness value of 3.0 to 9.0 $N/mm^2$ using hardness testing method BS 2782; PT3 Method 365D.

The bearing liner is preferably molded to the backing to form a single component and the backing can be made from polyurethane, for example Corothane 75D. Alternatively the backing can be made from carbon fiber reinforced plastics material, for example polybutyleneterphthlate (CFR-PBT), or an alloy of CFR-PBT with polyurethane. Again, the backing material can be made from polyetheretherketone (CFR-PEEK).

With yet another construction the backing material can be made from polymethylmethacrylate, all of these materials being suitable for molding. Preferably the bearing liner is made from Corothane 80A. Ideally the bearing liner will be bonded to the backing, but it may also be retained by a mechanical interlock between the two components.

As mentioned above, the element can be in the form of an acetabular cup. Thus, the embodiment shown in U.S. Pat. No. 5,609,646 the teachings of which are incorporated herein by reference, can be applied, that is, the backing may comprise a substantially part-spherical main portion and two independent arms projecting therefrom and formed by a separation or opening in the rim of the backing.

With this arrangement the inner bearing surface of the bearing liner is substantially part-spherical over a portion thereof spaced substantially opposite the separation or opening between the arms of the backing.

Preferably the bearing component has independent arms similar to the backing with a separation or opening between them and preferably the bearing component is of substantially the same configuration as the backing.

Alternatively the bearing component can be substantially hemispherical and extend across the separation or opening between the arms of the backing.

BRIEF DESCRIPTION OF THE DRAWINGS

The invention can be performed in various ways but one embodiment, as applied to an acetabular cup, will now be described by way of example and with reference to the accompanying drawings in which.

DETAILED DESCRIPTION

Figure 1:
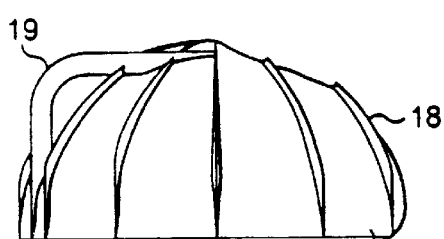
FIG. 1 is a side elevation of a prosthetic bearing element according to the invention.
Figure 2:
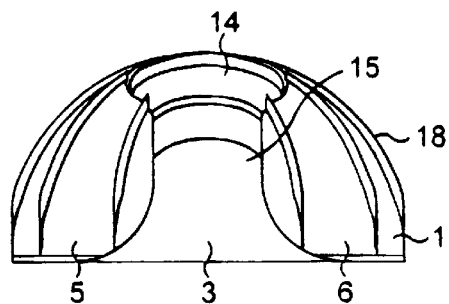
FIG. 2 is a front elevation of the element shown in FIG. 1.
Figure 3:
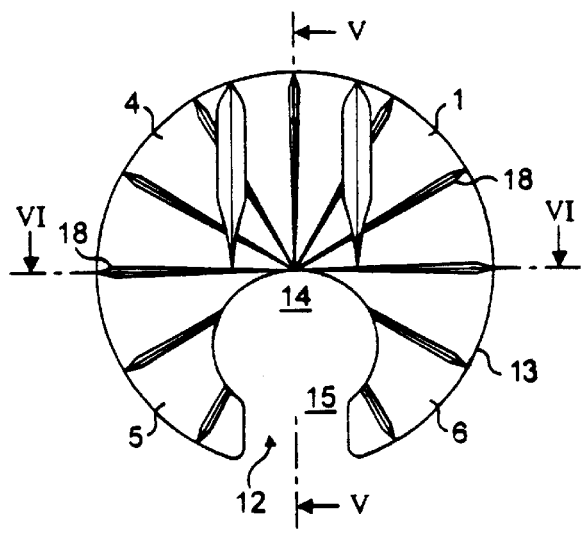
FIG. 3 is a plan view from above of the element shown in FIGS. 1 and 2.
Figure 4:
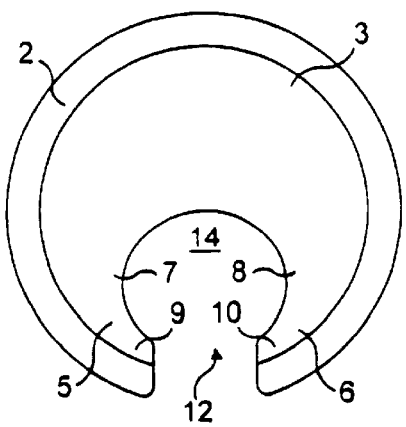
FIG. 4 is a plan view from below of the element shown in the preceding figures.
Figure 5:
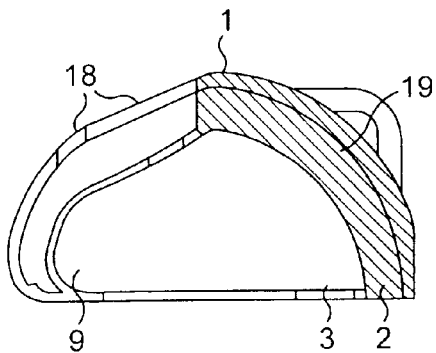
FIG. 5 is a cross-sectional side elevation on the line V—V of FIG. 3.
Figure 6:
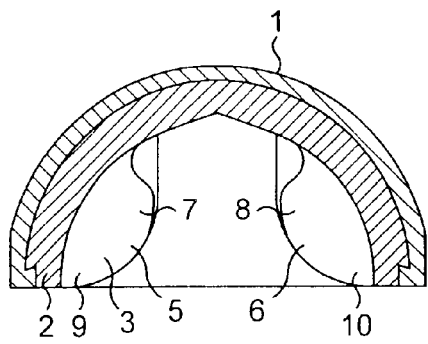
FIG. 6 is a cross-sectional view on the line VI—VI of FIG. 3.
Figure 7:
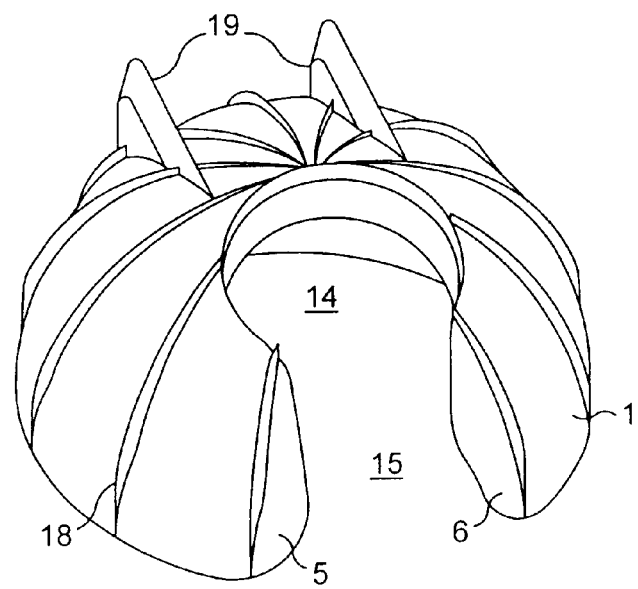
FIG. 7 is an isometric view from above of the element shown in the preceding figures.

As shown in the figures the cementless prosthetic bearing element according to the invention comprises a backing generally denoted as 1 which supports a bearing liner 2 (most clearly shown in FIGS. 5 and 6). The bearing liner 2 has a bearing surface 3. The backing is molded from a relatively rigid polymeric material, for example polyurethane in the form of Corothane 750D, CFR-PBT, CFR-PEEK or polymethylmethacrylate. The liner can be made from Corothane 80A and the liner and backing can be molded together by the technique described in U.S. Pat. No. 5,879,387, the liner being bonded to the backing by the molding process.

The general overall shape and construction of the prosthesis is similar to that described in U.S. Pat. No. 5,609,646, that is the main portion 4 of the backing is substantially part-spherical and there are two independent arms 5 and 6 which extend from the main part 4. The preferred external shape of the inner bearing liner 3 is also hemispherical and fits within the backing 1 but the preferred inner surface of the bearing component is only hemispherical over its main portion only it is relieved over inner surfaces 7 and 8 of its arms 9 and 10.

If desired the inner bearing liner 3 could be substantially hemispherical and merely carry a thin splitting line or slit to provide the two arms.

In the preferred embodiment arms 5 and 6 and 9 and 10 are spaced apart to provide a gap or opening 12 between them. The arms are spaced apart about an arc on the part-spherical main portion of the backing and the liner breaking out on the rim 13 and the arms themselves and the main portion are together substantially part-spherical.

Preferred backing 1 thus comprises a substantially part-spherical wall having a rim 13 which is interrupted by a shaped opening to provide two spaced apart arms 5 and 6.

In the preferred embodiment main part 14 of opening 12 is substantially semi-circular and has a mouth 15 which provides the interruption in rim 13 and which is of smaller width than remainder 14 of the opening. The backing 1 is therefore substantially horseshoe shaped.

Because of its construction and the materials used the backing are sufficiently flexible to accept deformation of the acetabulum of the patient but is stiffer than the inner bearing component.

It has been found that this particular shape of opening is convenient and successful and the loading is transferred into the pelvis as required, in particular this shape of opening ensures efficiently that no load is transferred into the bone as an undesired location.

Figure 8:
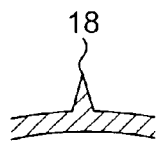
FIG. 8 is a cross-sectional view of a representative projecting strake on the outer surface of the bearing element.

In the preferred embodiment the outer surface of backing 1 includes a number of raised engagement features which are provided in directions extending away from and/or towards outer periphery 13 of the outer surface. Thus, the raised engagement features are in the form of projecting strakes 18 which extend radially from outer periphery 13 and are of triangular cross-section, as is most clearly shown in FIG. 8. Between the projecting strakes the surface is substantially part-spherical.

The preferred outer surface of backing 1 also carries a pair of projecting fins 19 which extend in spaced apart parallel chordal directions. The outer surface of the backing may be plasma sprayed with hydroxyapatite (HA) coating which is osteo-conductive and stimulates bone growth.

In order to insert the acetabular cup into an acetabulum, the bone is first prepared to the appropriate shape and a series of triangular grooves are carved into it by the surgeon which will line up with the strakes on the cup. Similarly two chordal grooves are cut to accept the fins 19.

The cup is now placed in position and lightly tapped, the strakes and fins holding it accurately as required. The joint is now reassembled and it has been found that the pressure of the ball of the femoral prosthesis, if such a prosthesis is used, or the natural ball shape of the bone, acts to pressurize the cup and hold it in position while bone growth takes place.

In the embodiment described the invention is applied to an acetabular cup but it can be applied to other types of prostheses in which its advantageous construction allows it to be used.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A cementless prosthetic bearing element comprising a backing which supports a bearing liner having a bearing surface, said backing being molded from a rigid polymeric material and said bearing liner being made from an elastomeric polyurethane material and to which said backing is molded with an outer surface which includes a number of raised engagement features in the form of radially extending stakes extending away from and/or towards the outer peripheral rim of the outer surface, wherein the backing outer surface is part spherical and said strakes extend continuously from the outer periphery of the rim towards a polar area of the backing and wherein said backing outer surface includes at least one fin intersecting at least one strake.

2. The cementless prosthetic bearing element as claimed in claim 1 wherein said strakes are of substantially triangular cross-section.

3. The cementless prosthetic bearing element as claimed in claim 1 wherein said outer surface is substantially part-spherical between the strakes.

4. The cementless prosthetic bearing element as claimed in claim 1 wherein said rigid polymeric material has a minimum hardness value of 65 N/mm$^2$ and said bearing liner is made from a "soft" elastomeric polyurethane material having a hardness value of 3.0 to 9.0 N/mm$^2$.

5. The cementless prosthetic bearing element as claimed in claim 1 wherein the bearing liner is made from Corothane 80A.

6. The cementless prosthetic bearing element as claimed in claim 1 wherein the bearing liner is bonded to the backing.

7. The cementless prosthetic bearing element as claimed in claim 1 wherein the bearing liner is retained on the backing by a mechanical interlock between the two components.

8. The cementless bearing element as set forth in claim 1 wherein said at least one fin extends from said outer surface a distance greater than said strakes.

9. The cementless prosthetic bearing element as claimed in claim 1 wherein said outer surface also carries one or more projecting fins which extend normal to the surface.

10. The cementless prosthetic bearing element as claimed in claim 9 wherein said fins can be spaced apart and extend in parallel chordal directions.

11. The cementless prosthetic bearing element as claimed in claim 10 wherein said polyurethane is Corothane 75D.

12. The cementless prosthetic bearing element as claimed in claim 1 wherein the bearing element is in the form of an acetabular cup.

13. The cementless prosthetic bearing element as claimed in claim 12 wherein said backing comprises a substantially part-spherical main portion and two independent arms projecting therefrom and formed by a separation or opening in the rim of said backing.

14. The cementless prosthetic bearing element as claimed in claim 13 wherein the inner bearing surface of the bearing element is substantially part-spherical over a portion thereof spaced substantially opposite the separation or opening between the arms of the backing.

15. The cementless prosthetic bearing element as claimed in claim 13 wherein the bearing element is substantially hemispherical and extends across the separation or opening between the arms of the backing.

16. The cementless prosthetic bearing element as claimed in claim 13 wherein the bearing element has two independent arms similar to the backing with a separation or opening between them.

17. The cementless prosthetic bearing element as claimed in claim 16 wherein said bearing component is of substantially the same configuration as the backing.

18. The cementless prosthetic bearing element as claimed in claim 1 wherein said liner is molded to said backing to form a single component.

19. The cementless prosthetic bearing element as claimed in claim 18 wherein said backing is made from carbon fiber reinforced polybutyleneterphthlate (CFR-PBT).

20. The cementless prosthetic bearing element as claimed in claim 18 wherein said backing material is made from polyetheretherketone (CFR-PEEK).

21. The cementless prosthetic bearing element as claimed in claim 18 wherein said backing material is made from polymethylmethacrylate.

22. The cementless prosthetic bearing element as claimed in claim 18 wherein said backing is made from polyurethane.

23. The cementless prosthetic bearing element as claimed in claim 22 wherein said polyurethane is Corothane 75D.

24. A cementless prosthetic bearing element comprising:
a polyurethane bearing liner having a bearing surface; and
a molded backing supporting said bearing liner on an inner surface thereof and an outer surface of said backing having integrally molded thereon a plurality of outwardly projecting strakes extending across said outer surface and at least one fin intersecting at least one strake, said at least one fin extending from said outer surface a distance greater than said strakes.

25. The cementless prosthetic bearing element as claimed in claim 24 wherein said rigid polymeric material has a minimum hardness value of 65 N/mm$^2$ and said bearing liner is made from a "soft" elastomeric polyurethane material having a hardness value of 3.0 to 9.0 N/mm$^2$.

26. The cementless prosthetic bearing element as claimed in claim 24 wherein said liner is molded to said backing to form a single component.

27. The cementless prosthetic bearing element as claimed in claim 24 wherein said backing is made from polyurethane.

28. The cementless prosthetic bearing element as claimed in claim 24 wherein the bearing liner is made from Corothane 80A.

* * * * *

UNITED STATES PATENT AND TRADEMARK OFFICE
CERTIFICATE OF CORRECTION

PATENT NO. : 6,758,864 B2
DATED : July 6, 2004
INVENTOR(S) : John Andrew Storer, Richard Eddy Field and Neil Rushton It is certified that error appears in the above-identified patent and that said Letters Patent is hereby corrected as shown below:

Column 1,
Line 17, after "example" insert -- , --.
Line 23, after "joint" insert -- , --.

Column 2,
Line 4, after "EP 0 297 789" insert -- , --.
Line 47, "is" should read -- are --.
Line 50, "teaching" should read -- teachings --.
Lines 60 and 62, after "example" insert -- , --.

Column 3,
Lines 35 and 37, cancel "of".
Line 55, after "example" insert -- , --.
Line 64, after "is" (first occurrence) insert -- , --.

Column 4,
Line 24, "are" should read -- is --.

Column 5,
Line 13, "stakes" should read -- strakes --.

Signed and Sealed this

Fifth Day of October, 2004

JON W. DUDAS
*Director of the United States Patent and Trademark Office*